US007186889B2

(12) United States Patent
Labate et al.

(10) Patent No.: US 7,186,889 B2
(45) Date of Patent: Mar. 6, 2007

(54) METHOD FOR GENETIC TRANSFORMATION OF WOODY TREES

(75) Inventors: Monica T. V. Labate, Piracicaba (BR); Carlos A. Labate, Piracicaba (BR); Esteban R. Gonzáles, Piracicaba (BR)

(73) Assignee: Suzano Bahia Sul Papel e Celulose S.A., Bahia (BR)

( * ) Notice: Subject to any disclaimer, the term of this patent is extended or adjusted under 35 U.S.C. 154(b) by 268 days.

(21) Appl. No.: 10/362,019

(22) PCT Filed: Aug. 16, 2001

(86) PCT No.: PCT/BR01/00103

§ 371 (c)(1), (2), (4) Date: Sep. 24, 2003

(87) PCT Pub. No.: WO02/14463

PCT Pub. Date: Feb. 21, 2002

(65) Prior Publication Data

US 2004/0055041 A1 Mar. 18, 2004

(30) Foreign Application Priority Data

Aug. 18, 2000 (BR) .................................... 0003908

(51) Int. Cl.
*C12N 15/82* (2006.01)
*C12N 15/87* (2006.01)
*A01H 5/00* (2006.01)

(52) U.S. Cl. ...................... 800/294; 800/298; 435/410; 435/419; 435/420; 435/430.1

(58) Field of Classification Search ................ 800/294, 800/298; 435/469, 410, 419, 420, 430.1
See application file for complete search history.

(56) References Cited

U.S. PATENT DOCUMENTS 5,693,512 A 12/1997 Finer et al.
6,211,432 B1 4/2001 Boudet et al.

FOREIGN PATENT DOCUMENTS

EP 1 050 209 A2 11/2000
WO WO 96/25504 8/1996

OTHER PUBLICATIONS

Moralejo, et. al., (Generation of transgenic Eucalyptus globules plantlets through Agrobacterium mediated transformation, Aust. J. Plant Physiol, 1998, vol. 25, pp. 207-212).*

Hansen et. al., 1999, Trends in plant Science, vol. 4, pp. 226-231, see p. 230.*

Potrykus, Gene Transfer to Cereals: An Assessment, 1990, Biotechnology, 8(6): 535-542.*

Narasimhulu et. al., 1996, The Plant Cell, Early transcription of Agrobacterium T-DNA genes in tobacco and maize, vol. 8, p. 874.*

Hood et. al. (Transgenic Research, vol. 2, pp. 208-218, 1993.*

Maunders M. J. ((1997) Genetic transformation of Eucalyptus species towards the modification of fibre characteristics. Proceedings Second International Wood Biotechnology Symposium, Canberra, Australia, Mar. 10-12, 1997).*

Harold N. Trick et al., Induction of Somatic Embryogenesis and Genetic Transformation of Ohio Buckeye (Aeculus Glabra Willd.), In Vitro Cellular and Developmental Biology-Plant, 1999, vol. 35, pp. 57-80.

Harold N. Trick et al., SAAT: sonication-assisted *Agrobacterium*-mediated transformation, Transgenic Research, 1997, vol. 6, pp. 329-336.

Harold N. Trick et al., Induction of Somatic Embryogenesis and Genetic Transformation of Ohio Buckeye (Aeculus Glabra Willd.), In Vitro Cellular and Developmental Biology-Plant, 1999, vol. 35, pp. 57-80.

Harold N. Trick et al., SAAT: sonication-assisted *Agrobacterium*-mediated transformation, Transgenic Research, 1997, vol. 6, pp. 329-336.

* cited by examiner

*Primary Examiner*—Elizabeth McElwain
*Assistant Examiner*—Georgia Helmer
(74) *Attorney, Agent, or Firm*—McDermott Will & Emery LLP

(57) ABSTRACT

The invention refers to a method to transform and obtain plants of woody trees, particularly *Eucalyptus spp.*, transformed by the introduction of exogenous genes of interest into their cells. The method makes use of sterilized seeds, which are co-cultivated with *Agrobacterium* cells containing a transference plasmid (tDNA), and any gene of interest. The method used for the transformation employs sonication to increase the efficiency of bacteria penetration within teguments and seed embryo tissues.

10 Claims, 2 Drawing Sheets
(2 of 2 Drawing Sheet(s) Filed in Color)

A

B

METHOD FOR GENETIC TRANSFORMATION OF WOODY TREES

FIELD OF THE INVENTION

The invention refers to a method to transform and obtain woody tree plants, particularly *Eucalyptus spp.*, transformed by the introduction of exogenous genes of interest into their cells. It also refers to the use of such transformed plants.

The method makes use of sterilized seeds, which are co-cultivated with *Agrobacterium*, cells containing a transference plasmid (tDNA) and any gene of interest. The technique used for the transformation utilizes sonication to increase the efficiency of bacteria penetration within teguments and embrionary tissues of the seeds.

This method for the genetic transformation of woody trees, particularly *Eucalyptus spp.*, belongs to the chemical technical field in the area of mutation or genetic engineering.

BACKGROUND OF THE INVENTION

As known, eucalyptus is widely planted in Asia, South America and some parts of Europe, especially in the Mediterranean region. This kind offers a range of advantages over other forest species for use in the cellulose industry, such as quick growing, regeneration from multiple sprouting after harvesting and capacity to grow in poor soils. Various research groups in many countries, including public and private institutions have attempted genetic transformation of eucalyptus. Few reports have however shown stable gene transference for different eucalyptus species.

Serrano et al., in their article "Genetic transformation of *Eucalyptus globulus* through biollistics: complementary development of procedures for organogenesis form zygotic embryos and stable transformation of corresponding proliferation tissue", *J. Exp. Botany* 47 (295), 1996, 285–290, discloses a particle bombing (bioballistic) method to introduce DNA molecules containing gene uidA coding the β-glucuronidase (GUS) protein into zygotic embryos of *Eucalyptus globulus*. After two months of bombing, callus were obtained which presented positive GUS reaction. Although tDNA integration was shown by hybridization through the Southern Blot method, plants were not regenerated.

Moralejo et al., "Generation of transgenic *Eucalyptus globulus* plantlets through *Agrobacterium tumefaciens* mediated transformation", *J. Plant Physiol.*, 25:297–212, 1998, obtained transgenic *E. globulus* plants by making use of the gene transference method via *Agrobacterium tumefaciens,* infecting plantlets which had been injured with micro-particles bombing before the co-culture. However, the efficiency in obtaining transgenic plants was very low, around 1%.

Mullins et al., "Regeneration and transformation of *Eucalyptus camaldulensis", Plant Cell Reports,* 16, 1997, 787–791, obtained plant regeneration from sprouts regenerated from foliar explants and transformation of a clone of *E. camaldulensis,* by making use of the transformation system as mediated by *Agrobacterium tumefaciens.*

Ho et al., "*Agrobacterium tumefaciens*—mediated transformation of *Eucalyptus camaldulensis* and production of transgenic plants", *Plant Cell Rep.*, 17, 1998, 675–680, also described the transformation and regeneration of *E. camaldulensis,* by making use of the *Agrobacterium* system to transform hypocotyls. In all these examples, low transformation efficiency was the main limiting factor to the large-scale use of such methods to introduce exogenous genes in eucalyptus.

Various methods have been used to optimize the efficiency of eucalyptus transformation by making use of the *Agrobacterium* system. Recently, a transformation system was developed using ultrasound and sonication to increase the efficiency of *Agrobacterium* penetration within target tissues for transformation. The method called SAAT ("Sonication Assisted *Agrobacterium* Transformation") was used to increase the efficiency of gene transference in soy, peas, wheat and corn (Trick & Finer, "SAAT-sonication assisted *Agrobacterium* mediated transformation", *Transg. Res.,* 6:329–336, 1997, "Sonicated assisted Agrobacterium mediated transformation of soybean [*Glycine max* (L.) Merrill] embryogenic suspension culture tissue", *Plant Cell Rep.,* 17:482–488, 1998, Santarém et al., "Sonication assisted Agrobacterium mediated transformation of soybean immature cotyledons: optimization of transient expression", *Plant Cell Rep.,* 17:752–759, 1998).

The use of ultrasound for plant tissues induces acoustic cavitation, generating microscopic injuries, which are channels to favor the internal exposure of tissues to *Agrobacterium* (Joersbo & Brunstedt, "Sonication: A new method for gene transfer to plants", *Physiol. Plant,* 85:230–234, 1992), thus increasing tDNA transitory expression levels. For eucalyptus, most tissues used for the genetic transformation are cotyledons, hypocotyls, immature embryos and callus obtained from different plant tissues.

A bioballistic or biollistic method is also known, consisting in firing micro-projectiles of gold or platinum containing precipitated DNA on their surfaces. The projectile goes through the cellular wall/membrane carrying DNA with it. To launch projectiles, equipment similar to a pressure rifle is used, in which pressure is produced by an inert gas. Such procedure is used for the genetic transformation of plants and animals.

Still on this issue, for chemical analysis procedures, ultrasonic wave generator systems are employed to prepare samples, be it in processes to extract chemical species or be it to dissolve solid samples. The base for ultrasonic application to such processes is related to the shock waves resulting from the application of an acoustic field over a material means. Such waves increase the interaction between the solvent and the surface of the solids, increasing the concentration of species present in the material being investigated in the solution. The vibration caused by ultrasounds minimizes the concentration gradient in the surroundings of the surface of the solid present in the exposed medium and makes possible the transport of salts and oxides from the surface of the solid to the solution. When ultrasound probes are employed, however, the association of magnetic agitators to the system should not be disregarded, as only a small zone of the solution, in which the probe is immersed, will be submitted to the high intensity produced by such processors and vigorous stirring provides the same level of interaction for the whole exposed solution.

In the sonication method, rupture of cells is obtained, thus allowing for gene introduction for the final genetic transformation. The use of sonication aims at increasing the transformation efficiency, since it causes injuries to the tissues, which then release phenol compounds, increasing the attraction of bacteria to those regions and facilitating gene transference.

The previously used bioballistic method for *Eucalyptus* did not encompass regeneration with β-glucuronidase (GUS) to the recovery of the final plant.

A method to use Agrobacterium with final regeneration into *E. camaldulensis* under low efficiency has also been reported.

Patent application WO 9625504-dated Aug. 22, 1996 describes a process to obtain transgenic plants by means of incorporation of a stable DNA sequence of interest. The process comprises cells or tissues of *Eucalyptus* with *Agrobacterium* being the mediator for the DNA sequence transference, inducing the formation of callus with phenyl urea derivatives in the presence of geneticin (G-418). The process is useful to transform clone material directly or indirectly derived from a mature *Eucalyptus tree.*

BRIEF DESCRIPTION OF THE INVENTION

Due to the limitations of all known methods so far, forbidding their use in large scale for the introduction of exogenous genes in eucalyptus, the present method has been studied, developed and arrived at, for the genetic transformation of woody trees, particularly, *Eucalyptus spp.* Said method, a fully new technique within this field of industrial activity, unexpectedly facilitates the genetic transformation of woody trees, particularly, *Eucalyptus spp.*

With this purpose, the method for genetic transformation of woody trees, particularly, *Eucalyptus spp.* at issue has as a main and undisclosed technical characteristic the genetic transformation via seeds of woody trees, particularly, *Eucalyptus spp.*, thus offering the possibility to increase substantially the efficiency of the process.

DESCRIPTION OF FIGURES

The file of this patent contains at least one drawing executed in color. Copies of this patent or patent application publication with color drawing(s) will be provided by the Patent and Trademark Office upon request and payment of the necessary fee.

These and other objects of this invention will be apparent to the one skilled in the art from the attached schematic figures, where.

DEFINITIONS

Figure 1:
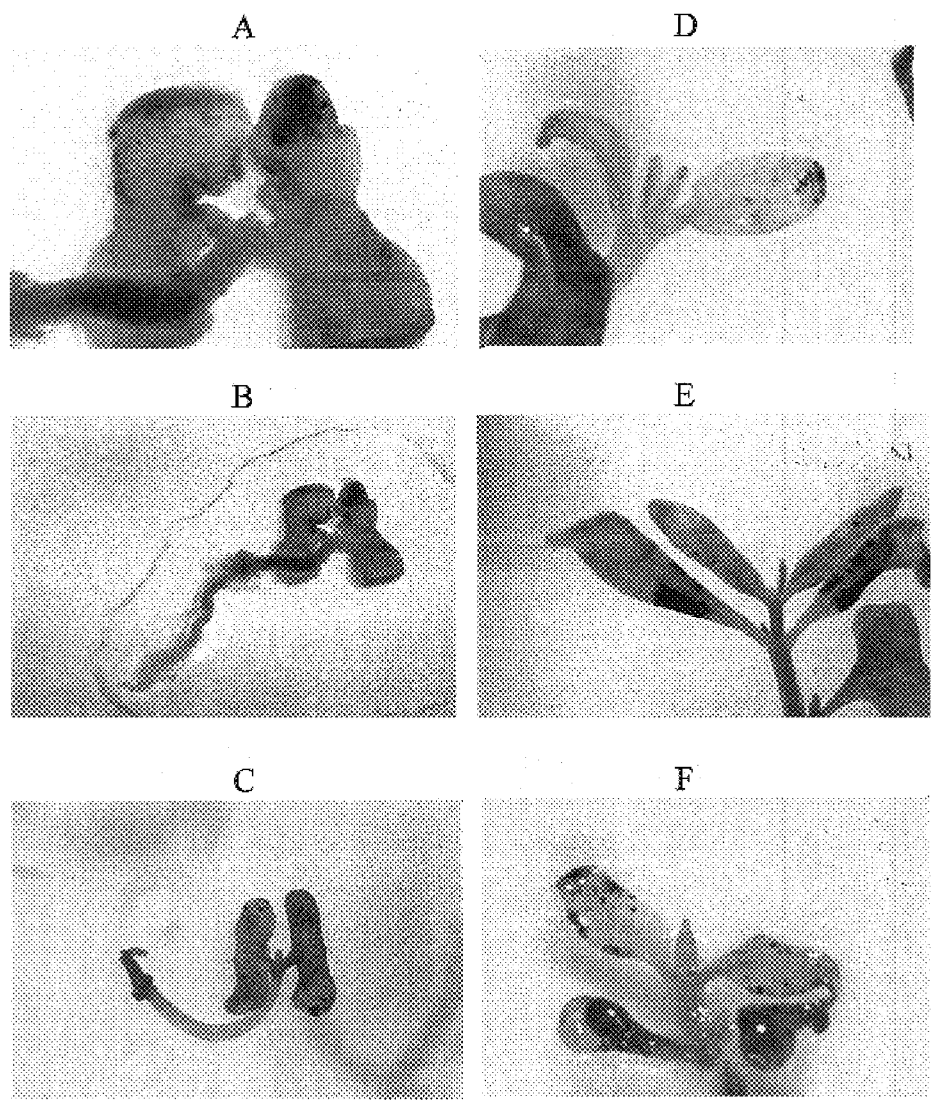
FIG. 1 is a view of the expression of β-glucuronidase (GUS) gene in 2-day germination seeds (A to C) and 15-day plantlets (D to F)

As used herein, with no limitation to the scope of the invention and unless expressly mentioned otherwise, the words below have the following meaning:

Hypocotyl=small plant stem below cotyledons.

Cotyledon=embryo leaf which may or may not contain nutritive stocks.

Leaf=lateral organ representing a laminar expansion of stem.

Seed=result of the development of ovule after being fertilization.

Plantlet=small rooted stem or germinated embryo.

Callus=mass of non-differentiated cells within higher plants which can be formed from cultivated cells or naturally as a reaction to an injury or infection.

Marker gene=gene which effects are observable over the organism.

β-Glucuronidase (GUS)=enzyme coding marker gene.

Col or collect or transition zone=intermediate region between the root and the stem, with small dimensions. It is an anatomically important region, since it is where a gradual reorganization of conducting tissues occurs, when radial (or root) beams become collateral, bicollateral or concentric beams.

t-Student=the t-Student test is a parametric hypothesis test to determine whether a given result is or is not statistically significant.

Explant=organ or part of a plant tissue used to start a culture "in vitro".

Auxin=class of growth hormones which cause cell elongation, apical dominance, root initiation (rooting), etc. Indol acetic acid (LAA) is a commonly used auxin in tissue culture.

MS Medium=Murashige & Skoog, "A revised medium for rapid growth and bioassays with tobacco tissue cultures", *Physiol. Plantarum,* 15:473–497, 1962;

MSW=MS Macro and Micro-nutrients with vitamins from the medium of White, "A handbook of plant tissue culture", *Lancaster,* 1943;

MS+BAP=as per Machado et al., "*Agrobacterium* strain specificity and shooty tumor formation in eucalyptus (*E. grandis×E. urophylla*)", *Plant Cell Rep.,* 16:299–303, 1997;

MM=multiplication medium;

MA=elongation medium;

ME=rooting medium;

Medium A, Medium B, Medium C=as per Serrano et al., "Genetic transformation of *Eucalyptus globulus* through biollistic: complementary development of procedures for organogenesis form zygotic embryos and stable transformation of corresponding proliferation tissue", *J. Exp. Botany* 47 (295), 1996;

G=as per Gonçalves, "Reversion to juvenility and cloning of *Eucalyptus urophylla* S. T., Blake in cell in tissue culture systems". *In: Symposium IUFRO em melhoramento genético e produtividade de espécies florestais de rápido crescimento,* pp.25–30, 1980, Brazil.

DETAILED DESCRIPTION OF THE INVENTION

The invention refers to a method to insert any gene of interest within woody trees, particularly, *Eucalyptus spp.*, by making use of seeds as a route for transference.

According to the invention, as a generic view, seeds are used at the start of germination, when an intense cell division activity occurs within cotyledonary leaves, thus favoring penetration of bacteria *Agrobacterium*. Once developed, the plantlet is cut off and callus are produced from the cotyledons which, with the addition of antibiotics, herbicides or other compounds to the media of culture, are selected to regenerate transformed plants.

The method of the invention deals with the generic introduction of a gene, i.e. any gene of interest. Final characteristics of the plant will depend on the gene being inserted. With no limitation to the scope of the invention, the following examples can be mentioned:

a gene granting resistance to a herbicide has as a final result a plant which is tolerant to a given herbicide;

a gene coding a protease inhibiting protein will generate as a final product a plant resistant to the attack of given pests.

A description of the final product can be made depending only on the characteristics of the gene of interest. Genes changing a phenotypic characteristic of interest can be introduced.

The introduced characteristics may or may not be found in a natural plant. A test of the method of the invention consisted in the introduction of the gene Lhch1*2 of peas within transgenic tobacco plants, resulting in an increase in biomass. The confirmation of the efficiency and applicability of the method resulted in an experiment using woody trees, such as *Eucalyptus spp.*, objects of this application.

The use of the sonication method with introduction through *Agrobacterium* was therefore developed for the genetic transformation of woody trees, particularly, *Eucalyptus spp.*, more specifically within difficult to regenerate species such as *E. grandis, E. urophylla* and hybrid *E. grandis×E. urophylla* (HGU), thus obtaining better efficiency.

The method object of the invention consists of the following steps (*Eucalyptus spp.* is being mentioned for ease of explanation, but it is well understood that this method applies to woody trees in general):

- sterilization of *Eucalyptus spp.* seeds, e.g. with ethanol and sodium hypochlorite and washing thereof;
- transference of such seeds to an appropriate medium of culture;
- germination for a period between it enters about 2 to 17 days;
- collection of germinated material;
- inoculation with *Agrobacterium*, particularly *Agrobacterium tumefaciens,* containing gene(s) of interest and optionally marker gene(s), under concentration of about $10^7$ to $10^9$ cells per ml;
- await inoculation between about 20 to 30 hours in a liquid medium;
- transference of the material to a solid medium for a period between about 38 and 50 hours in the dark, under temperature between about 25 to 31° C. and ambient humidity;
- transference of the material to start the plantlet growing step in the light;
- removal of a plantlet leaf obtained between about 5 and 17 days during growing step in the light;
- transference of the plantlet leaf to the MS medium containing auxins derived from urea, particularly phenyl urea;
- await germination of the plant tissue for approximately 20 days;
- identification and selection of transformed plantlets;
- keeping the transforming plantlets in a culture and elongation medium for about 20 days;
- regeneration of the final plant as transformed from one of the following regions: hypocotyl; cotyledon; primary leaves and col.

Optionally, after the seed germination step, the collected material can be sonicated for a period of between about 30 and 90 seconds, before the inoculation with *Agrobacterium.*

The method described in the invention is different from previous methods for employing seeds, whose essential purpose is to favor genetic transformation. A large number of individuals can therefore be infected, substantially increasing the efficiency of the process.

Added to this, the invention also encompasses the further inclusion of a seed sonication step, leading to an even greater final regeneration from the hypocotyl, a region that presents a greater regeneration rate according to the process. Hypocotyl has a regeneration rate higher than 40% and the sonication step raises the rate of transforming regions, for instance, from the level of 1 to 17% up to 4 to 37%.

The result is a final regeneration rate, which is higher than that obtained by previous methods.

The selection step of regenerated plants is obtained by means of using of markers, usual in biotechnological methods, which are introduced within the *Agrobacterium* together with the gene of interest, leading to the confirmation of efficiency of this method and allowing a differentiation in transformed plants, which is an important fact for a large-scale production process.

By means of the invention, final transgenic plants as obtained have innumerous applications, such as:

- increase in biomass;
- change in lignin percentage;
- stronger protection against pests and diseases;
- stronger resistance to water deficit;
- change in the chemical composition of wood (e.g. lignin, hemicellulose, cellulose, extracts);
- physical change of wood; such as basic density of the wood and/or bark;
- resistance to herbicides;
- use of the plant, in whole or in part, in paper and cellulose industry, transformation of wood, building and fuel.

DESCRIPTION OF SPECIFIC EMBODIMENTS OF THE INVENTION

Preparation of Means for Tissue Culture

*E. grandis, E. urophylla* and hybrid *E. grandis×E. urophylla* (HGU) seeds were disinfected by making use of the following protocol:

Wash in ethanol at approximately 70% for about 1 min, wash with sterilized water, transfer to sodium hypochlorite (around 8% volume/volume) and Tween (non-ionic surfactant derived from sorbitan ester) (around 0.1% v/v) for about 10 min; after this treatment, the material was washed for four times under sterilized water. Seeds germinated on Petri dishes containing MS culture medium. Table 1 presents various culture media as used in different experiments.

TABLE 1

Culture media used to regenerate different plant tissues:

| Components | MS | MM | ME | MA | Medium 1 | Medium 2 |
|---|---|---|---|---|---|---|
| Macro-nutrients | MS | MS | G | MS | ½MS | ½MS |
| Micro-nutrients | MS | MS | G | MS | MS | MS |
| Na/Fe EDTA | MS | MA | 1,5 MS | MS | MS | MS |
| Vitamins | MS | White | G | White | MS | MS |
| Sucrose (%) | 2.0 | 2.0 | 2.0 | 2.0 | 2.0 | 2.0 |
| pH | 5.8 | 5.8 | 5.8 | 5.8 | 5.8 | 5.8 |
| BAP | — | 0.2 mg/l | — | 0.1 mg/l | — | — |
| NAA | — | 10 μg/l | — | — | 0.465 mg/l | 0.465 mg/l |
| IBA | — | — | 1.0 mg/l | 0.2 mg/l | — | — |
| AGAR (%) | 0.6 | 0.6 | 0.6 | 0.6 | 0.6 | 0.6 |
| Phenyl urea | — | — | — | — | 0.5 mg/l | 1.0 mg/l |

Preparation of Inoculation of Agrobacterium Tumefaciens Strain LBA 4404

A colony of this strain was inoculated into liquid Rhizo medium with about 100 $mg.L^{-1}$ of Kanamicin and cultivated under stirring at approximately 200 rpm for a period of about 48 h, until the grown bacteria reached optical density of about 1–5×10$^8$ cells.mL$^{-1}$. The cells were centrifuged at approximately 5000 rpm for about 10 min and the pellet was re-suspended in a liquid MS medium containing approximately 100 mM of ketoseringone. The bacteria suspension was used for seed inoculation.

Protocol to Transform Seeds by Means of Sonication

The method described below makes use of the Agrobacterium system to transform seeds. Added to that method, sonication is applied as a pre-treatment of seeds for *Agrobacterium* infection, according to the works of Sawahel, "Ultrasound-mediated stable transformation of potato tuber discs", *Biotech. Techniq.,* 10:821–824, 1996, Trick & Finer 1997, 1998 and Santarém et al. 1998. Tissue sonication causes a series of micro-injuries on the external epidermis surface and tegument tissues, thus facilitating bacteria penetration and the exposure of embryo tissues.

Seeds were sterilized as previously described, transferred to Petri dishes containing MS medium with approximately 3% sucrose, and kept within controlled growth chambers with photo-periods of about 16 h of light and 8 h in the dark, under temperature of about 26° C. Seeds germinated within various time intervals (0, 2, 5, 15 and 17 days) were sonicated within periods of about 30 to 90 seconds before being inoculated with the strain LBA 4404 containing β-glucuronidase (GUS) gene under the control of the 35S promoter of cauliflower mosaic virus (CaMV). Sonication was performed with seeds immersed in about 35 ml of liquid MS medium in a 100 ml magenta glass flask, using a frequency of about 40 Hz. After sonication, seeds were inoculated in a liquid medium (MS) with *Agrobacterium tumefaciens* (LBA 4404), under density of about 10$^7$ to 10$^9$ cells per ml for a period of about 24 h under constant stirring (approximately 100 rpm). Control seeds (not sonicated) were transferred immediately after sterilization to the inoculation medium. After the inoculation treatment, seeds were transferred to Petri dishes, containing solid MS medium, for co-cultivation for a period of approximately 48 h, at a temperature of about 28° C. in the dark. Seeds have been subsequently washed with sterilized water containing about 200 mg.L$^{-1}$ of cefotaxim, dried over sterilized filter paper and transferred to solid MS medium containing about 100 mg.L$^{-1}$ of cefotaxim. After a time period of about 7 to 10 days from the complete seed germination, plantlets were evaluated for the expression of β-glucuronidase (GUS) gene. The transformation efficiency considered two parameters: percentage of sprouts with at least a blue point and the transformation gradient. This last parameter represents the average of blue points (transformed areas) from the total of transformed sprouts. The transformation gradient indicates the efficiency of transformation.

Statistical delineation was performed with random blocks with two repetitions for each treatment. 50 seeds were used per treatment, but not all seeds germinated. Averages were compared with the t-Student test for 5% probability. Table 2 presents results of seed transformation by making use of the sonication system followed by infection by *Agrobacterium*.

TABLE 2

Effect of sonication on the transformation rate of *E. grandis* seeds. Figures followed by different letters indicate significance ($P < 0.05$) on the t-Student test. Figures in parenthesis indicate standard average deviation.

| | Control a | | Sonicated b | |
|---|---|---|---|---|
| Days of germination | % transformed regions | Transformation Rate | % transformed regions | Transformation rate |
| 0c | 2.17 (1.53) | 2.0 (1) | 4.02 (1.52) | 2.0 (1) |
| 2b | 14.0 (4.0) | 4.18 (1.93) | 21.72 (0.72) | 5.93 (0.33) |
| 5d | 1.51 (1.51) | 1.5 (1.5) | 5.54 (2.34) | 2.83 (1.83) |
| 15a | 17.14 (2.86) | 1.12 (0.12) | 37.38 (6.61) | 2.27 (0.27) |
| 17b | 11.0 (1.9) | 1.12 (0.12) | 19.54 (1.89) | 4.0 (1) |

Figure 2:
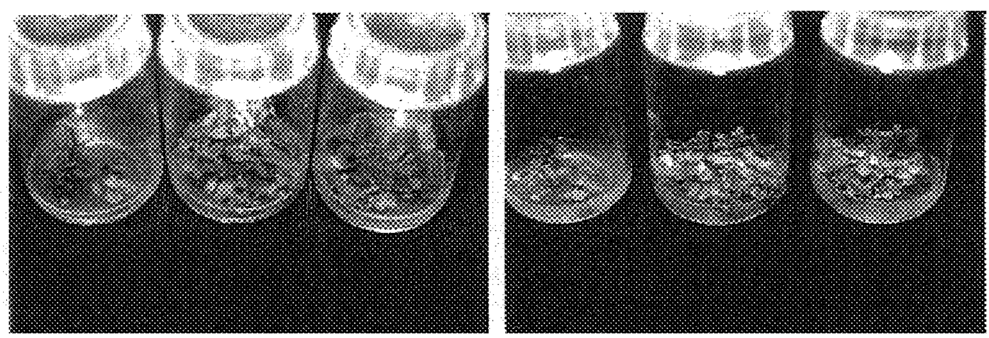
FIG. 2 shows the regeneration of explants from hypocotyls, cotyledons and leaves, as obtained by the use of phenyl urea (Medium 1), where one can see: (A) formation of sprouts, and (B) elongation of sprouts.

Results from this experiment show the potential to transform seeds and plantlets, with the positive sonication effect increasing seed transformation efficiency. Sonicated seeds with 2 and 15 days of germination presented higher transformation rates (21.7 and 37.38%, respectively). There was a differential response from transformed regions, depending on the age of the seed. For seeds germinated for two days, around 90% of blue segments were located in the cotyledons and in the col region (between hypocotyl and roots) while, in seeds germinated for five days, about 70% of the β-glucuronidase activity was located in the cotyledons (FIG. 2, A to C). On the other hand, in the plantlets with about 15 to 17 days, about 60% of transformed regions occurred in the first couple of leaves (FIG. 1, D to F).

Regeneration Systems for Transformed Tissues

Transformed tissue regeneration is an important step for the process of exogenous-to-plant gene transference. Two examples of regeneration systems, which can be employed to regenerate, transformed tissues such as cotyledons and primary leaves are described below.

Embodiments that illustrate the invention will now be supplied, not presenting limiting characteristics.

EXAMPLE 1

Tissue regeneration was obtained with the use of a phenyl urea, by adjusting concentrations for each species of eucalyptus, from approximately 0.5 to about 1.0 mg.L$^{-1}$ (Medium 1 and Medium 2, respectively). Seeds of *E. grandis* and the hybrid HGU were germinated for 20 days under MS medium. Cotyledons, first pair of leaves, hypocotyls and the col of each plantlet were subsequently extracted. Such explants were transferred to media 1 and 2 in equal parts.

Explants were cultivated for a period of approximately 30 days under dark conditions, renewing the medium every about 15 days. After that period, they were transferred to a sprouting induction medium in a culture chamber with a photo-period of about 16 h light/8 h darkness, for about 20 days. The medium used to induce sprouting was Medium 3 (see Table 1) containing about 0.2 mg.L$^{-1}$ of phenyl urea. The material remained in the sprouting-inducing medium for a period of approximately 20 days. After that period, it was transferred to a multiplication medium (MM) for about 20 days and subsequently to an elongation medium (MA). Evaluations were made based on the quantity of sprouts as formed in both species. In this case, differences in regeneration rates between both genotypes were not considered. For each treatment, 13 explants from hybrid HGU and 26 explants from *E. grandis* were used. Results show that the formation of sprouts was higher under the dosage of about 0.5 mg.L$^{-1}$ of phenyl urea (Medium 1), 27.3%, while the sprout formation rate for Medium 2 was 16.1%, considering the total quantity of used explants for both genotypes. Sprout regeneration rate as considered for each tissue for both genotypes was: cotyledons 16.2%; primary leaves 35.7%; hypocotyls 43.59% and col 2.3%.

EXAMPLE 2

Based on previous results, plant regeneration was only obtained for Medium 1, which presented the highest sprout formation rate. Plant material used was the same. Seeds were sterilized as described in the previous example, being transferred to Petri dishes containing MS medium for about two days, under photo-period of approximately 16 h of light and temperature of about 26° C. Germinated seeds were sonicated for a period of about 30 seconds before being inoculated with LBA 4404 strain containing β-glucuronidase gene and NPTII gene for resistance against Kanamicin and geneticin G-418. Sonication was performed with seeds immersed in approximately 35 ml of liquid MS medium in a magenta flask. After sonication, they were inoculated in a liquid medium (MS) with *Agrobacterium* (see Example 1), for a period of approximately 24 hours under constant stirring (aprox.100 rpm). After inoculation treatment, seeds were transferred to Petri dishes containing solid MS medium for co-cultivation for a period of about 48 hours, under temperature of around 28° C. in the dark. Seeds were subsequently washed with sterilized water containing about 200 mg.L$^{-1}$ of cefotaxim, dried over sterilized filter paper and transferred to solid MS medium containing approximately 100 mg.L$^{-1}$ of cefotaxim, where they stayed for a period of about 15 days, thus allowing for plantlet development.

From each plantlet, cotyledons were taken off and transferred to Medium 1 with approximately 0.5 mg.L$^{-1}$ of phenyl urea, about 100 mg.L$^{-1}$ of Kanamicin and about 100 mg.L$^{-1}$ of cefotaxim, kept in the dark for about 30 days. The medium was renewed approximately every 15 days. Plantlets were subsequently transferred to the same medium, containing about 10 mg.L$^{-1}$ of geneticin G-418 and about 100 mg.L$^{-1}$ of cefotaxim under light, to induce sprouting, for about 30 days. In that medium, the material is subject to strong selection, with survival rate varying among used species from about 70 to 90%. Callus and sprouts appearing from such treatment were transferred to multiplying medium (MM) containing about 10 mg.L$^{-1}$ of geneticin G-418, about 100 mg.L$^{-1}$ of cefotaxim, for a period of approximately 20 days, when most sprouts died. Remaining live sprouts were transferred to MA medium until they reached a length of about 3 to 4 cm. They were subsequently transferred to ME medium for about ten days in the dark and then transferred to a growing chamber for an approximate period of 20 days. Plant acclimatization took place in a greenhouse, in a mixture of earth and vermiculite.

Table 3 presents percentage data of sprout formation for *E. grandis* and the hybrid *E. grandis*×*E. urophylla* (HGU).

TABLE 3

SPROUT FORMATION PERCENTAGE

| Plant Structures | *E. grandis* | HGU |
|---|---|---|
| Hypocotyls | 25.0 ± 8.4 | 29.2 ± 4.2 |
| Cotyledons | 20.8 ± 4.2 | 24.5 ± 3.7 |
| Leaves | 10.4 ± 2.1 | 8.3 ± 4.2 |

Other embodiments of the invention will be readily perceived by one skilled in the art from the disclosure included in the presented description or with the practice of the invention as disclosed herein. It is stressed that the examples as presented are particular embodiments of the invention, whose true scope is expressed by the attached claims.

The invention claimed is:

1. A method for genetic transformation of *Eucalyptus spp*., which comprises the following steps:

sterilization and washing of seeds of *Eucalyptus spp* trees;

transference of said seeds to an appropriate medium of culture;

germination for a period between about 2 and 17 days;

collection of germinated material;

inoculation with *Agrobacterium*, containing one or more genes of interest and optionally one or more marker genes, under concentration between about $10^7$ and $10^9$ cells per ml;

inoculation between about 20 and 30 hours in a liquid medium;

transference of the material to a solid medium for a period between about 38 and 50 hours in the dark, under temperature between about 25 and 31° C. and ambient humidity;

transference of the material to start plantlet growth in the light;

withdrawal of a plantlet leaf obtained between about 5 and 17 days during growth in the light;

transference of the plantlet leaf to the a MS medium containing phenyl urea;

germination of the plant tissue for approximately 20 days; and identification and selection of the transformed plantlets.

2. A method for genetic transformation of *Eucalyptus spp*., which comprises the following steps:

sterilization and washing of seeds of *Eucalyprus spp* trees; transference of said seeds to an appropriate medium of culture;

germination for a period between about 2 and 17 days;

collection of germinated material;

sonication of the material as collected;

inoculation with *Agrobacterium*, containing one or more genes of interest and optionally one or various marker genes, under concentration between about $10^7$ and $10^9$ cells per ml;

inoculation between about 20 and 30 hours in a liquid medium;

transference of the material to a solid medium for a period between about 38 and 50 hours in the dark, under temperature between about 25 and 31° C. and ambient humidity;

transference of the material to start the plantlet growth in the light;

withdrawal of a plantlet leaf obtained between about 5 and 17 days during growth in the light;

transference of the plantlet leaf to the MS medium containing auxins derived from urea;

germination of the plant tissue for approximately 20 days; and identification and selection of transformed plantlets.

3. The method according to claims 1 or 2, characterized by the fact that the gene or genes of interest are chosen from a gene granting resistance to herbicides, coding a protease inhibiting protein or changing a phenotypic characteristic of interest.

4. The method according to claims 1 or 2, characterized by the fact that the gene or genes of interest are chosen from NPTII of resistance to Kanamicin and geneticin G-418 and Lhcbl*2.

5. The method according to claims 1 or 2, characterized by the fact that the marker gene is β-glucuronidase (GUS).

6. A method for genetic transformation of *Eucalyptus spp*., which comprises the following steps:

sterilization and washing of seeds of *Eucalyptus spp trees;* transference of said seeds to an appropriate medium of culture;

germination for a period between about 2 and 17 days;

collection of germinated material;

inoculation with *Agrobacterium*, containing one or more genes of interest and optionally one or more marker genes, under concentration between about $10^7$ and $10^9$ cells per ml;

inoculation between about 20 and 30 hours in a liquid medium;

transference of the material to a solid medium for a period between about 38 and 50 hours in the dark, under temperature between about 25 and 31° C. and ambient humidity;

transference of the material to start the plantlet growth step in the light;

withdrawal of a plantlet leaf obtained between about 5 and 17 days during growth in the light;

transference of plantlet leaf to the a MS medium containing phenyl urea;

germination of the plant tissue for approximately 20 days;

identification and selection of transformed plantlets;

maintaining transforming plantlets in a multiplication and elongation medium for about 20 days;

regeneration of the final transformed plant from one of the following regions: hypocotyl; cotyledon; primary leaves and intermediate region between root and stem.

7. The method according to claim 6, characterized by the fact that seed sterilization is performed with ethanol and sodium hypochlorite.

8. The method according to claim 6, characterized by the fact that the seeds are chosen from *Eucalyptus grandis, Eucalyptus urophylla* and hybrid *Eucalyptus grandis*×*Eucalyptus urophylla* (HGU).

9. The method according to claim 6, characterized by the fact that said *Agrobacterium* is *Agrobacterium tumefaciens.*

10. A genetically transformed *Eucalyptus spp.*, obtained by the method as in any one of claims 1, 2 or 6, wherein said *Eucalyptus spp.* is a hybrid *Eucalyptus grandis*×*Eucalyptus urophylla* (HGU).

* * * * *